United States Patent [19]

Kawada et al.

[11] Patent Number: 4,689,404

[45] Date of Patent: Aug. 25, 1987

[54] PRODUCTION OF CYTOSINE NUCLEOSIDES

[75] Inventors: Mitsuru Kawada, Amagasaki; Kiyoharu Matsumoto, Kawachinagano; Masaaki Tsurushima, Minoo, all of Japan

[73] Assignee: Takeda Chemical Industries, Ltd., Osaka, Japan

[21] Appl. No.: 831,441

[22] Filed: Feb. 20, 1986

[30] Foreign Application Priority Data

Mar. 5, 1985 [JP] Japan .................................. 60-44219

[51] Int. Cl.[4] ........................................... C07H 19/06
[52] U.S. Cl. ..................................................... 536/23
[58] Field of Search ..................................... 536/23, 24

[56] References Cited

U.S. PATENT DOCUMENTS 3,328,388  6/1967  Shen et al. ............................ 536/23
4,423,212 12/1983  Skulnick .............................. 536/23

OTHER PUBLICATIONS

J. Org. Chem., 39, 3654–3674 (1974).
Synthesis, 1981, 748.
Journal of the American Chemical Society, 79, 5060–5064 (1957).
Chemical & Pharmaceutical Bulletin 25, 3347–3353 (1977).

Primary Examiner—Johnnie R. Brown
Assistant Examiner—John W. Rollins, Jr.
Attorney, Agent, or Firm—Wenderoth, Lind & Ponack

[57] ABSTRACT

A cytosine nucleoside is produced by reacting a peracylcytosine with a hydroxy-protected monosaccharide or a hydroxy-protected nucleoside whose base moiety is other than cytosine and, if necessary, removing the hydroxy-protecting group.

3 Claims, No Drawings

PRODUCTION OF CYTOSINE NUCLEOSIDES

This invention relates to a new method for producing cytosine nucleosides which are of value as drugs or synthetic intermediates thereof.

Cytosine nucleosides are not only the main constituents of nucleic acids but also compounds of use as drugs or synthetic intermediates thereof. Cytidine, in particular, is an important starting material for synthesis of cytidine diphosphate choline (general name: citicoline) [refer to e.g. J. Org. Chem., 34, 1547–1550 (1969); Chem. Pharm. Bull., 19, 2466–2471 (1971)].

A variety of methods are known for the synthesis of pyrimidine nucleosides such as cytidine and the most prevalent of such synthetic methods comprises condensing a trimethylsilyl-protected pyrimidine base with a protected sugar in the presence of a Lewis acid and, then, deprotecting the condensate [for example, U. Niedballa and H Vorbrüggen, J. Org. Chem., 39, 3654–3674 (1974) and A. Matsuda, Y. Kurasawa and K. A. Watanabe, Synthesis, 1981, 748.]. However, the above method is disadvantageous in that the protective trimethylsilyl group is moisture-labile and the silylating agent as such is also unstable to moisture and expensive.

This invention provides an industrially advantageous method for producing cytosine nucleosides which overcomes the above-mentioned disadvantages of the prior art technology.

More particularly, this invention relates to a method for producing a cytosine nucleoside which comprises reacting a peracylcytosine with a hydroxy-protected monosaccharide or a hydroxy-protected nucleoside whose base is other than cytosine and, if necessary, removing the hydroxy-protecting group.

The essential characteristic of this invention resides in using a peracylated cytosine as a starting compound.

When the present inventors selected, as a cytosine-protecting group which is not decomposed by moisture, a carboxylic acid-derived acyl group (specifically, acetyl or benzoyl) and reacted the corresponding $N^4$-acylcytosine with a hydroxy-protected 1-O-acetylribofuranose in the presence of a Lewis acid, the reaction proceeded only in low yield to their surprise. With the thought that this low reactivity was occasioned by the substantial insolubility of the cytosine protected with such acyl group in the Friedel-Crafts reaction solvent and the weak nucleophilicity of the nitrogen atom in the 1-position of cytosine, the present inventors conducted a further study and unexpectedly found that peracylated cytosine compounds are highly soluble in Friedel-Crafts reaction solvents and that when such a peracylcytosine compound is reacted with hydroxy-protected 1-O-acetylribofuranose in the presence of a Lewis acid, the condensation reaction proceeds in high yield without involving difficulties in handling. The findings were followed by further studies which have resulted in completion of this invention.

As the peracylcytosine there may be used any compound derived from cytosine by substitution with two or more acyl groups. The acyl groups are preferably carboxylic acid-derived acyl groups.

Among such peracylcytosines, preferred are $N^4,O^2$-diacylcytosines and $N^4,N^4,O^2$-triacylcytosines of the formula

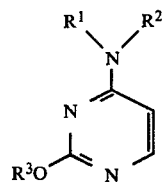

wherein $R^1$ and $R^2$ each is a carboxylic acid-derived acyl group or one of $R^1$ and $R^2$ is a carboxylic acid-derived acyl group and the other is a hydrogen atom and $R^3$ is a carboxylic acid-derived acyl group.

The carboxylic acid-derived acyl group represented by $R^1$, $R^2$ or $R^3$ in the above formula [I] may be an aliphatic or aromatic acyl group. The aliphatic acyl group may be either straight or branched and includes, amoung others, acetyl, propionyl, butyryl, isobutyryl, pentanoyl, hexanoyl, heptanoyl, octanoyl, nonanoyl and decanoyl. Among them, preferred are alkanoyl groups containing 3–16 carbon atoms, more preferably 4–8 carbon atoms. Examples of the aromatic acyl group are benzoyl, naphthoyl and substituted benzoyl and naphthoyl groups in which the substituent or substituents are selected from among halogen atoms, lower alkyl groups, hydroxy group, groups derived from hydroxy by substitution (e.g. methoxy, ethoxy, acetoxy), amino group, groups derived from amino by substitution, acyl groups, carboxyl group, lower alkoxycarbonyl groups, and so forth. Among these carboxylic acid-derived acyl groups, there are preferred those aromatic acyl groups mentioned above, especially benzoyl.

As the monosaccharide, there may be used any monosaccharide capable of serving as a nucleoside constituent. As such, there may be mentioned pentoses and hexoses such as D-ribofuranose, D-arabinofuranose, D-deoxyribofuranose, D-ribopyranose, D-glucopyranose, D-glucofuranose, D-galactopyranose, D-mannopyranose and D-talopyranose. Preferred among these monosaccharides are pentoses such as D-ribofuranose, D-ribopyranose and 3'-deoxy-D-ribofuranose. More particularly, the use of D-ribofuranose is advantageous.

In accordance with the invention, the above monosaccharide is combined, at the 1-position thereof, with the peracylcytosine, so that the hydroxy groups at other positions which should not participate in the reaction are protected in advance. As the protective group, there may be used any group capable of protecting sugar hydroxy groups. Examples are those carboxylic acid-derived acyl groups detailedly mentioned in relation to the peracylcytosine, and isoalkylidene groups (e.g. isopropylidene). Among them preferred are lower alkanoyl groups containing about 2–6 carbon atoms and benzoyl, more preferably lower alkanoyl groups, in particular acetyl.

Although said monosaccharide may be subjected to the reaction in the free form with respect to its 1-position hydroxy group, it is preferable to use it in the 1-O-acylated, 1-O-alkylated or 1-halide form. As the acyl group in said 1-O-acylated form, there may be mentioned, for instance, those carboxylic acid-derived acyl groups detailedly mentioned with respect to the peracylcytosine, with lower alkanoyls of 2–6 carbon atoms, in particular acetyl, and benzoyl being preferred. As the alkyl group in said 1-O-alkylated form, there may be mentioned methyl, ethyl, propyl, isopropyl, n-butyl, isobutyl, n-pentyl, isopentyl, n-hexyl and the like, with lower alkyl groups of 1–4 carbon atoms being preferred. The halogen in said 1-halide form may be any of fluorine, chlorine, bromine and iodine but is preferably chlorine or bromine.

The nucleoside, whose base moiety is other than cytosine, may be a purine or pyrimidine nucleoside and advantageously has the monosaccharide mentioned above as the constituent sugar. Particularly preferred are uridine, inosine and guanosine.

The nucleoside is subjected to the reaction in the form in which its sugar hydroxy groups are protected. Preferred as the protective groups are those mentioned hereinabove as the protective groups for monosaccharides.

The reaction between the peracylcytosine and the hydroxy-protected monosaccharide or nucleoside whose base moiety is other than cytosine is carried out in an appropriate solvent in the presence of a Lewis acid. The peracylcytosine and the monosaccharide or nucleoside are submitted to the reaction generally in equimolar proportions to give satisfactory results. The mole ratio may be modified as necessary, however. As the Lewis acid, there may be used any one which has FriedelCrafts catalyst activity. Suitable examples are inorganic acids (sulfuric acid, hydrochloric acid, etc.), strong organic acids (p-toluenesulfonic acid, trifluoroacetic acid, trifluoromethanesulfonic acid, fluorosulfonic acid, etc.), metal halides such as stannic chloride, titanium tetrachloride, aluminum chloride, ferrous chloride, zinc chloride, zinc bromide and zinc iodide, boron trifluoride etherate, and trialkylsilyl esters of strong acids [trimethylsilyl trifluoromethanesulfonate ($CF_3SO_3SiMe_3$), bistrimethylsilyl sulfate ($Me_3Si-OSO_2OSiMe_3$), trimethylsilyl trifluoroacetate ($CF_3CO_2SiMe_3$), etc.]. This reaction is conducted in an appropriate solvent that is generally used in Friedel-Crafts reaction. Thus, it may be any solvent that does not interfere with the reaction. For example, halogenated hydrocarbons such as dichloromethane, 1,2-dichloroethane, tetrachloroethane, etc., carbon disulfide, acetonitrile and so on may be used. The reaction temperature may range from 0° C. to near the reflux temperature of the solvent used and preferably in the range of 0° C. to room temperature, although the reaction may be conducted at a still higher or lower temperature for the purpose of controlling the reaction velocity. There are cases in which purging the reactor with an inert gas (for example, nitrogen gas or argon gas) suppresses occurrence of side reactions and leads to an increased yield.

In the method of this invention, the object cytosine nucleotide compound is produced by condensation reaction when a peracylcytosine is reacted with a hydroxy-protected monosaccharide or by sugar transfer reaction when a peracylcytosine is reacted with a nucleoside other than hydroxy-protected cytosine. Generally, the protective groups on the sugar moiety remain on and the acyl group in the $O^2$-position of cytosine base has been removed in the product cytosine nucleoside. When a peracylcytosine having two acyl groups in the $N^4$-position is used in the reaction, there are cases, depending on reaction conditions, in which only one of the acyl groups has been removed in the reaction product.

The cytosine nucleoside thus produced can be easily separated from the Friedel-Crafts catalyst in the conventional manner and, if desired, deprotected. For removal of the Friedel-Crafts catalyst, an appropriate procedure corresponding to the reaction conditions used can be utilized. For example, aqueous washing and treatment with an excess of alkali or acid in the presence of water may be mentioned. Removal of protective groups can be accomplished by the per se known procedures which vary with different kinds of protective groups. For example, when the protective group to be removed is a carboxylic acid-derived acyl group, the conventional alkali hydrolysis [for example, see Journal of The American Chemical Society, 79, 5060–5064 (1957), the disclosure of which is incorporated herein by reference] or a method analogous thereto may be followed to remove the acyl group on the cytosine base as well as the particular protective group at a time to thereby give the unsubstituted cytosine nucleoside e.g. cytidine. In this case, the protected cytosine nucleoside need not be purified but the reaction product mixture, as it is or after partial purification, is advantageously treated with alkali.

The cytosine nucleoside thus prepared can be separated and purified by the conventional procedures such as recystallization, adsorption or ion exchange column chromatography, and so on.

The sugar transfer from a pyrimidine base to a purine base is a known reaction but the sugar transfer from a purine base to a pyrimidine base or from one pyrimidine base to another pyrimidine base, as it takes place when a nucleoside is reacted in this invention, is a new reaction not found in the literature.

Of the peracylcytosine used in accordance with this invention, $N^4,O^2$-diacylcytosines and $N^4,N^4,O^2$-triacylcytosines of general formula [I]are novel compounds not found in the literature and can be easily prepared by reacting a reactive derivative of a carboxylic acid corresponding to the particular acyl group with cytosine in an appropriate solvent in the presence of a base.

More particularly, said reactive derivative of carboxylic acid used for the above acylation reaction may for example be the acid halide, acid anhydride or active ester compound, and preferably is the acid halide. The base may be any basic compound that acts as an acid acceptor, and preferably is pyridine, trialkylamine (e.g. triethylamine; briefly Et3N), potassium carbonate or the like. The solvent may be any solvent that does not interfere with the reaction. Thus, mention may be made of halogenated hydrocarbons such as dichloromethane, 1,2-dichloroethane, tetrachloroethane, etc., hydrocarbons such as hexane, benzene, toluene, etc., ethers such as diethyl ether, dioxane, tetrahydrofuran, etc., acetic acid esters such as ethyl acetate, etc., acetonitrile, N,N-dimethylformamide, dimethyl sulfoxide, hexamethylphosphoramide, and so on. Generally preferred is a solvent having a boiling point higher than the reaction temperature, for example 1,2-dichloroethane or toluene. The reaction temperature is generally about 50° to 200° C. and preferably about 70° to 120° C., although the reaction may be conducted at a still higher or lower temperature for the purpose of controlling the reaction velocity. The acylating agent used in this acylation of cytosine is generally used in a proportion of 2 to 6 mole equivalents with respect to cytosine and about 2 to 3 mole equivalents is sufficient.

The production of $N^4,O^2$-benzoylcytosine and $N^4,N^4,O^2$-tribenzoylcytosine, for example, may be schematically shown below.

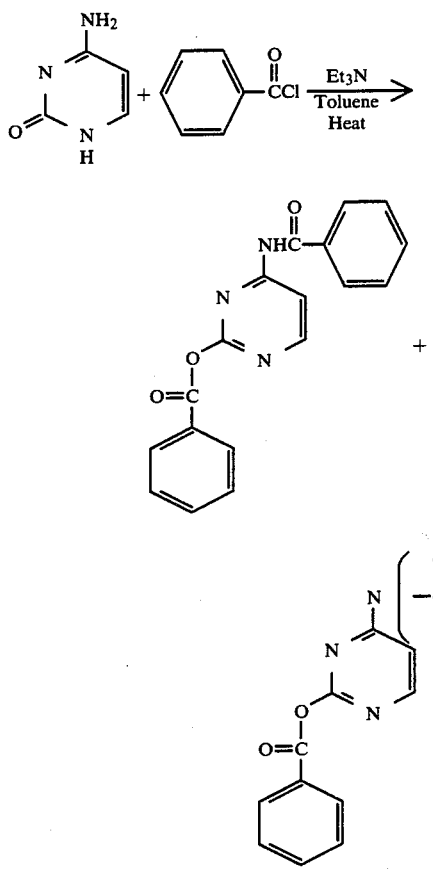

The resulting peracylcytosine need not be isolated but the reaction product mixture (which may contain a small amount of the monoacyl compound) may be directly reacted with the monosaccharide or nucleoside. Thus, as will be seen from Example 5 given hereinafter, the present invention provides an integral process for production of cytidine in high yield starting from cytosine with simple procedures.

In accordance with this invention, cytosine nucleosides can be produced in high yield by reacting a peracylcytosine, which is stable against moisture and easy to handle, with a hydroxy-protected monosaccharide or a hydroxy-protected nucleoside whose base moiety is other than cytosine.

The following Examples and Reference Examples are further illustrative but by no means limitative of the present invention.

EXAMPLE 1

In 1,2-dichloroethane (15 ml) is dissolved $N^4,O^2$-dibenzoylcytosine (1.38 g) and 1,2,3,5-tetra-O-acetyl-$\beta$-D-ribofranose (2.56 g) followed by addition of TiCl$_4$ (2.15 g) with stirring at room temperature. The mixture is stirred at room temperature for 15 hours, at the end of which time it is poured in ice-water. To this is added CHCl$_3$ and the mixture is stirred and filtered with a filtration aid. After phase separation, the organic layer is washed with water, dried and concentrated under reduced pressure. To the residue is added methanolic aqueous ammonia (methanol: 25% aqueous ammonia=3:1, 20 ml) and the mixture is heated at 60° C. for 5 hours. The reaction mixture is concentrated under reduced pressure and methanol (10 ml) is added to the concentrate. The mixture is allowed to stand at room temperature overnight, whereupon colorless crystals of cytidine separate out. Yield 0.944 g (94.5%, overall yield from dibenzoylcytosine), m.p. 215°–216° C. Elemental Analysis: Calcd. for C$_9$H$_{13}$N$_3$O$_5$: C, 44.45; H, 5.39; N, 17.28. Found C:44.60; H, 5.87; N, 17.34.

EXAMPLE 2

In 1,2-dichloroethane (50 ml) is dissolved $N^4,O^2$-dibenzoylcytosine (5.0 g) and 1,2,3,5-tetra-O-acetyl-$\beta$-D-ribofuranose (5.1 g) followed by addition of a solution of SnCl$_4$ (4.15 g) in 1,2-dichloroethane (40 ml) with stirring at 0° C. The mixture is stirred at 0° C. for 5 minutes and then at room temperature overnight. The reaction mixture is poured in ice-water and after addition of CHCl$_3$ and stirring, the mixture is filtered with a filtration aid. After phase separation, the organic layer is washed with water, dried, and concentrated under reduced pressure. To the residue is added ethanol and the mixture is allowed to stand at room temperature overnight, whereupon 2′,3′,5′-tri-O-acetyl-$N^4$-benzoylcytidine separates out as colorless needles. Yield 6.32 g (85.3%), m.p. 180.5°–182.5° C. Elemental Analysis: calcd. for C$_{22}$H$_{23}$N$_3$O$_9$: C, 55.81; H, 4.90. Found: C, 56.06; H, 4.92; N, 8.84.

EXAMPLE 3

In 1,2-dichloroethane (40 ml) is dissolved $N^4,O^2$-dibenzoylcytosine (1.64 g) and 1,2,3,5-tetra-O-acetyl-$\beta$-D-ribofuranose (1.92 g) followed by addition of CF$_3$SO$_3$SiMe$_3$ (1.28 g) with stirring at 0° C. The reaction mixture is poured in ice-water and extracted with 1,2-dichloroethane. The extract is washed with water, dried, and concentrated under reduced pressure. To the residue is added methanol (20 ml) and, then, concentrated NH$_4$OH (10 ml), and the mixture is allowed to stand at room temperature for 3 days. The reaction mixture is concentrated under reduced pressure and ethanol is added to the residue, whereupon cytidine is obtained as colorless crystals. Yield 1.13 g (90.4%, overall yield from dibenzoylcytosine).

EXAMPLE 4

In 1,2-dichloroethane (10 ml) is dissolved $N^4,N^4,O^2$-tribenzoylcytosine (90 mg) and 1,2,3,5-tetra-O-acetyl-$\beta$-D-ribofuranose (90 mg), followed by addition of a solution of SnCl$_4$ (200 mg) in 1,2-dichloroethane (20 ml) at 0° C. with constant stirring. The reaction mixture is stirred at 0° C. for 20 minutes and then, at room temperature for 2 hours, at the end of which time it is poured in ice-water. To this is added CHCl$_3$ and after mixing, the mixture is filtered with a filtration aid. After phase separation, the organic layer is washed with water, dried, and concentrated under reduced pressure. To the residue is added isopropanol and the mixture is allowed to stand at room temperature overnight to give 2′,3′,5′-tri-O-acetyl-$N^4$-benzoylcytidine as colorless needles. Yield 60 mg (59.4%).

EXAMPLE 5

A mixture of cytosine (11.11 g), benzoyl chloride (36.4 g), Et$_3$N (26.3 g) and 1,2-dichloroethane (300 ml) is stirred on reflux for 5 hours. The reaction mixture is cooled to 10° C. and the precipitated Et$_3$N.HCl is filtered off. To the filtrate is added 1,2,3,5-tetra-O-acetyl-$\beta$-D-ribofuranose (31.8 g) followed by addition of TiCl$_4$ (34.15 g) with stirring at room temperature. The mixture is stirred at room temperature overnight and, then, poured in ice-water. It is mixed with CHCl₃ and filtered with a filtration aid. After phase separation, the organic layer is washed with water, dried, and concentrated under reduced pressure. To the residue are added methanol (300 ml) and concentrated NH₄OH (100 ml) and the mixture is stirred at 60°–65° C. for 5 hours. The reaction mixture is concentrated under reduced pressure and methanol is added to the residue for crystallization, whereby cytidine is is obtained as colorless needles. Yield 20 g (82.3%).

EXAMPLE 6

To a solution of SnCL₄ (0.9 g) in 1,2-dichloroethane (60 ml) is added a solution of 2',3',5'-tri-O-acetylinosine (0.87 g) and $N^4,O^2$-dibenzoylcytosine (1.04 g) in 1,2-dichloroethane (40 ml) with stirring at room temperature. The mixture is stirred at 80° C. overnight. After cooling to room temperature, the reaction mixture is poured in ice-water. To this is added CHCl₃ and the mixture is filtered with a filtration aid. After phase separation, the organic layer is washed with water, dried, and concentrated under reduced pressure. To the residue is added water to make a total of 10.00 g. As assayed by high performance liquid chromatography (HPLC), 77.9 mg of cytidine is obtained.

EXAMPLE 7

To a solution of 2',3',5'-tri-O-acetylguanosine (0.94 g) and $N^4,O^2$-dibenzoylcytosine (0.78 g) in 1,2-dichloroethane (50 ml) is added a solution of SnCl₄ (1.08 g) in 1,2-dichloroethane (10 ml) with stirring at room temperature. The mixture is stirred at room temperature for 50 minutes, at 80° C. for 4 hours and at 70° C. overnight. After cooling to room temperature, the reaction mixture is poured in ice-water, mixed with CHCl₃ and filtered with a filtration aid. After phase separation, the organic layer is washed with water, dried, and concentrated under reduced pressure. To the residue are added methanol (30 ml) and concentrated NH₄OH (4 ml) and the mixture is stirred at 70° C. for 6 hours. The reaction mixture is concentrated under reduced pressure and water is added to residue to make a total of 20.0 g. As assayed by HPLC, 73.4 mg (27.0%) of cytidine is obtained.

EXAMPLE 8

CF₃SO₃SiMe₃ (2.6 g) is added to a solution of $N^4,O^2$-dibenzoylcytosine (3.19 g) and 1,2,3,4-tetra-O-acetyl-β-D-ribopyranose (3.6 g) in 1,2-dichloroethane (40 ml) with stirring at room temperature. The mixture is stirred at room temperature for 3 days, after which it is poured in ice water and extracted with CHCl₃. The extract is washed with water and concentrated under reduced pressure. To the residue is added methanol (15 ml) and concentrated NH₄OH (15 ml) and the mixture is allowed to stand at room temperature overnight. The mixture is then concentrated under reduced pressure and ethnol is added to the residue. Along the mixture to stand at 5° C. overnight gives colorless needles of β-pyranosylcytosine. Yield 1.26 g (52%), m.p. 289°–291° C. (decomp.). Elemental Analysis: Calcd. for C₉H₁₃N₃O₅.H₂O: C, 41.38; H, 5.79 N, 16.06. Found: C, 41.36; H, 6.06; N, 15.98.

EXAMPLE 9

In 1,2-dichloroethane (50 ml) is dissovled $N_4,O^2$-dibenzoylcytosine (3.19 g) and 2,3,5-tri-O-acetyl-D-rebofuranosyl chloride (3.0 g) followed by addition of TiCl₄ (3.4 g) with stirring at room temperature. The mixture is stirred at room temperature overnight and it is poured in ice-water, mixed with CHCl₃ and filtered with a filtration aid. After phase separation, the organic layer is washed with water, dried, and concentrated under reduced pressure. To the residue are added methanol (60 ml) and concentrated NH₄OH (20 ml) and the mixture is heated at 60° C. for 5 hours. The reaction mixture is concentrated under reduced pressure and ethanol (40 ml) is added to the residue. The mixture is allowed to cool and stand at room temperature overnight, whereupon cytidine separates out as colorless needles. Yield 1.6 g (65.8%).

EXAMPLE 10

In 1,2-dichloromethane (50 ml) is dissolved $N^4,O^2$-dibenzoylcytosine (3.19 g) and 2,3,5-tri-O-acetyl-D-ribofuranosyl bromide (3.0 g) followed by addition of TiCl₄ (3.4 g) with stirring at room temperature. The mixture is stirred at room temperature overnight and it is poured in ice-water, mixed with CHCl₃ and filtered with a filtration aid. After phase separation, the organic layer is washed with water, dried, and concentrated under reduced pressure. To the residue are added methanol (60 ml) and concentrated NH₄OH (20 ml) and the mixture is heated at 60° C. for 5 hours. The reaction mixture is concentrated under reduced pressure and methanol (20 ml) is added to the residue. The mixture is allowed to stand at 5° C. overnight to give colorless needles of cytidine. Yield 1.4 g (57.6%).

EXAMPLE 11

TiCl₄ (1.71 g) is added to a mixture of $N^4,N^4,O^2$-tribenzoylcytosine (2.1 g) and methyl D-ribofuranoside (1.93 g) and 1,2-dichloroethane (60 ml) with stirring at room temperature. The mixture is stirred at 30° C. for 7 hours and, then, at 20° C. for 4 days. Thereafter, the reaction mixture is poured in ice-water, mixed with CHCl₃ and filtered with a filtration aid. After phase separation, the organic layer is washed with water, dried, and concentrated under reduced pressure. To the residue is added methanol (30 ml) and concentrated NH₄OH (10 ml), and the mixture is heated at 70° C. for 5 hours. The reaction mixture is concentrated under reduced pressure and water is added to the residue to make 50.02 g. As assayed by HPLC, 0.502 g (41.8%) of cytidine is obtained.

REFERENCE EXAMPLE 1

A mixture of cytosine (5.6 g), benzoyl chloride (15.0 g), Et₃N (20 ml) and toluene (150 ml) is heated with stirring at 100° C. for 4 hours. After cooling, the insolubles are filtered off and the filtrate is concentrated under reduced pressure. To the residue is added toluene-diisopropyl ether and the insoluble powder (mainly a mixture of dibenzoylcytosine and tribenzoylcytosine) is collected by filtration. This insoluble powder is subjected to flash column chromatograpy using silica gel (230–400 mesh) and hexane-ethyl acetate (3:2, /v). The first emerging fraction gives colorless needles of $N^4,O^2$-dibenzoylcytosine. Yield 7.0 g (43.5%), m.p. 139°–141° C.; IR$\nu_{max}^{KBr}$cm$^{-1}$=3350 (NH), 1730, 1700 (C=O); ¹H-NMR (CDCl₃)δ: 8.77 (lH, broad s., NH), 8.65 (lH, d, J=6 Hz, 6-vinyl H), 8.27 (lH, d, J=6 Hz, 5-vinyl H), 8.3–7.1 (llH, m, aromatic H). Elemental Analysis: Calcd. for C₁₈H₁₈N₃O₃: C, 67.71; H, 4.10; N, 13.16. Found: C, 67.71; H, 4.12; N, 13.15.

The structure of this compound is also confirmed by X-ray crystallographic analysis.

The succeeding eluate yields colorless needles of $N^4,N^4,O^2$-tribenzoylcytosine (recrystallized from toluene). Yield 5.0 g (23.5%), m.p. 151.0°–152.5° C.; IR $\nu_{max}^{KBr}cm^{-1}$ = 1755, 1710 (C=O). $^1$H-NMR (CDCl$_3$)⊕: 8.68 (lH, d, J=6 Hz, 6-vinyl H), 8.2–7.15 (16H, m, 5-vinyl H and aromatic H). Elemental Analysis: Calcd. for C$_{25}$H$_{17}$N$_3$O$_4$: C, 70.92; H, 40.5; N, 9.92. Found: C, 70.76; H, 3.93; N, 9.83.

The structure of this compound is also confirmed by X-ray crystallographic analysis.

REFERENCE EXAMPLE 2

A mixture of cytosine (11.41 g), benzoyl chloride (50.12 g), Et$_3$N (65 ml) and toluene (400 ml) is heated at 100° C. for 6 hours. After cooling, the insolubles are filtered off and the filtrate is concentrated under reduced pressure. The residue is triturated with toluene and diisopropyl ether to give crude $N^4,N4,O^2$-tribenzoylcytosine. Yield 23.56 g (54.3%).

REFERENCE EXAMPLE 3

In methanol (50 ml) is dissolved 2',3',5'-tri-O-acetyl-$N^4$-benzoylcytidine (0.53 g) followed by addition of concentrated NH$_4$OH (5 ml) with stirring at 70° C. The mixture is stirred at 70° C. for 2.5 hours, at the end of which time ethanol is added. The mixture is allowed to stand at room temperature overnight to give colorless needles of cytidine. Yield 0.26 g (95.6%).

What is claimed is:

1. A method for producing cytidine, which comprises reacting (a) $N^4,O^2$-dibenzoylcytosine, (b) $N^4,N^4,O^2$-tribenzoylcytosine or (c) a mixture of (a) and (b) with 1,2,3,5-tetra-O-lower alkanoyl-β-D-ribofuranose in a solvent in the presence of a Lewis acid having Friedel-Crafts catalyst activity at a temperature of from about 0° C. to near the reflux temperature of the solvent used to obtain 2',3',5'-tri-O-lower alkanoyl-$N^4$-benzoylcytidine and subjecting the 2',3',5'-tri-O-lower alkanoyl-$N^4$-benzoylcytidine to alkali hydrolysis to obtain cytidine.

2. A method according to claim 1, wherein 1,2,3,5-tetra-O-lower alkanoyl-β-D-ribofuranose is 1,2,3,5-tetra-O-acetyl-β-D-ribofuranose.

3. A method according to claim 1, wherein cytosine is reacted with benzoyl halide in the presence of a base to obtain a perbenzoylcytosine mixture, reacting the perbenzoylcytosine mixture with 1,2,3,5-tetra-O-acetyl-β-D-ribofuranose in the presence of TiCl$_4$, SnCl$_4$ or CF$_3$SO$_3$SiMe$_3$ at a temperature of from about 0° C. to about room temperature to obtain 2',3',5'-tri-O-acetyl-$N^4$-benzoylcytidine to alkali hydrolysis to obtain cytidine.

* * * * *

UNITED STATES PATENT AND TRADEMARK OFFICE
CERTIFICATE OF CORRECTION

PATENT NO. : 4,689,404

DATED : August 25, 1987

INVENTOR(S) : MITSURU KAWADA ET AL.

It is certified that error appears in the above-identified patent and that said Letters Patent is hereby corrected as shown below:

Column 7, line 69, change "$N_4$" to --$N^4$--.

Column 9, line 5, change "⊕" to --$\delta$--.

Column 10, line 24, after "$N^4$-benzoylcytidine" insert --and subjecting 2',3',5'-tri-O-acetyl-$N^4$-benzoylcytidine--.

Signed and Sealed this

Twenty-third Day of February, 1988

Attest:

DONALD J. QUIGG

*Attesting Officer*         *Commissioner of Patents and Trademarks*